(12) United States Patent
Tyszkiewicz

(10) Patent No.: US 6,318,371 B1
(45) Date of Patent: Nov. 20, 2001

(54) MOUTH GUARD FOR MEDICAL USE

(75) Inventor: Tadeusz Tyszkiewicz, Kristianstad (SE)

(73) Assignee: Inoris Medical AB, Limhamn (SE)

( * ) Notice: Subject to any disclaimer, the term of this patent is extended or adjusted under 35 U.S.C. 154(b) by 0 days.

(21) Appl. No.: 09/507,252

(22) Filed: Feb. 18, 2000

(30) Foreign Application Priority Data

Feb. 19, 1999 (SE) .................................................. 9900576

(51) Int. Cl.⁷ ..................................................... A61C 5/14
(52) U.S. Cl. ...................... 128/859; 128/861; 128/207.14
(58) Field of Search .................................. 128/846, 848, 128/859–862, 207.14; 602/902

(56) References Cited

U.S. PATENT DOCUMENTS

| | | |
|---|---|---|
| 4,640,273 | 2/1987 | Greene et al. . |
| 4,944,313 | 7/1990 | Katz et al. . |
| 5,203,324 * | 4/1993 | Kinkade ........................... 128/207.14 |
| 5,533,523 * | 7/1996 | Bass ...................................... 128/859 |
| 5,590,643 * | 1/1997 | Flam ................................ 128/207.14 |

FOREIGN PATENT DOCUMENTS 2 711 320    4/1995   (FR) .

* cited by examiner

*Primary Examiner*—Michael A. Brown
(74) *Attorney, Agent, or Firm*—Merchant & Gould P.C.

(57) ABSTRACT

A mouth guard for medical use is made of nonrigid plastic material and comprises a U-shaped portion forming a through opening to receive an instrument therein. The opening is shaped as a keyhole having a wider portion and a narrower portion that is open at one side of the mouth guard. Radially protruding flanges are provided at the ends of the annular portion. The instrument can be introduced laterally into the wider portion of the keyhole through the narrower portion under resilient yielding of the U-shaped portion.

7 Claims, 1 Drawing Sheet

MOUTH GUARD FOR MEDICAL USE

Applicants hereby claim the benefit under Title 35, United States Code §119 of foreign priority of Sweden application Ser. No. 9900576-1, filed Feb. 19, 1999, which is hereby incorporated by reference.

BACKGROUND OF THE INVENTION

1. Field of the Invention

The invention relates to a mouth guard for medical use which forms a through opening to receive therein an instrument, and forms radially protruding flanges at each end for positioning the mouth guard in the mouth.

Preferably, the mouth guard is a disposable product.

Such mouth guards are used together with a diagnostic instrument, such as an endoscope, in order to protect the instrument against damage. The mouth guard is located between the teeth. One flange is positioned in front of the teeth or the palate in case the patient has false teeth and these have been removed, in order to restrict displacement of the mouth guard backwards, while the other flange is positioned behind the teeth or the palate, respectively, and restricts displacement forwards.

2. Description of the Prior Art

Most mouth guards available today are shaped as a closed oval or circle. US-A-4,640,273 discloses a mouth guard of this type which comprises a relatively hard plastic core with a relatively soft plastic coat to cushion the patient's bite so that the mouth guard is less uncomfortable in use and lessons the likelihood of injury to the patient, delicate parts of the instrument still being protected. A mouth guard of closed configuration cannot be applied when the instrument is already located in the mouth. It is necessary to position the mouth guard in the mouth before the instrument is introduced into the mouth and passed into the esophagus or the stomach.

FR-A-2,711,320 describes a ring-shaped mouth guard of resilient material which forms a normally closed slot in order that the instrument can be introduced into the mouth guard laterally by the ring being opened at the slot under yielding of the elastic material.

A primary object of the invention is to facilitate positioning of the mouth guard in the mouth when the instrument is already positioned in the esophagus or the stomach.

Another object is to provide the necessary protection of the patient and the instrument without the necessity to make the mouth guard of a composite material.

BRIEF SUMMARY OF THE INVENTION

In order to achieve said objects the invention provides a mouth guard of the kind referred to, comprising a U-shaped portion forming a through opening to receive an instrument therein, said opening being shaped as a keyhole having a wider portion and a narrower portion open at one side of the mouth guard; and radially protruding flanges at each end of the annular portion for positioning the mouth guard in the mouth said U-shaped portion and said flanges being made in their entirety of nonrigid plastic material to allow the instrument to be introduced laterally into the keyhole through the narrower portion under resilient yielding of the U-shaped portion and then to be received in the wider portion.

The mouth guard can be mounted on the instrument by pressing the mouth guard at the open narrower portion of the keyhole against the instrument so that the instrument can be passed through said narrower portion under elastic yielding of the limbs formed by the U-shaped portion and then to be received by the wider portion wherein the instrument is then maintained. Thus, it is not necessary to open a passage for the instrument before it can be received by the wider portion.

BRIEF DESCRIPTION OF THE DRAWING

An illustrative embodiment of the invention will be described below with reference to the accompanying drawing in which.

DETAILED DESCRIPTION OF THE INVENTION

Figure 4:
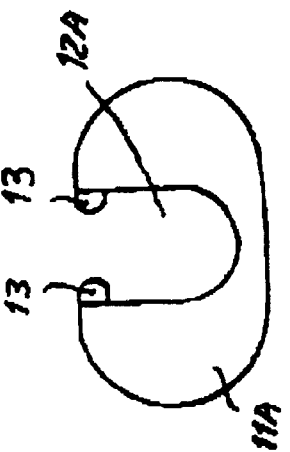
FIG. 4 is an end view of the mouth guard as seen from the other end thereof.
Figure 3:
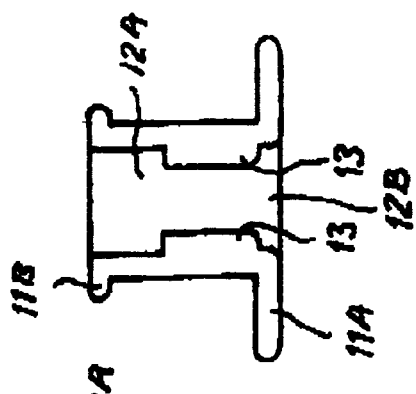
FIG. 3 is a side view of the mouth guard as seen from the side thereof wherein the keyhole opens.
Figure 2:
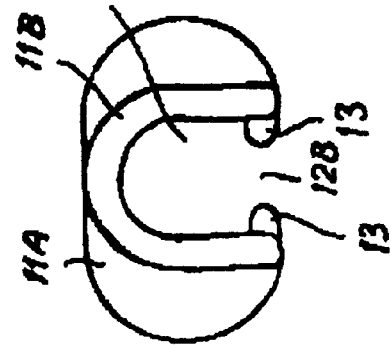
FIG. 2 is an end view of the mouth guard am seen from one end thereof.
Figure 1:
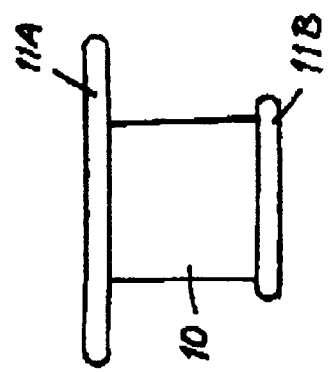
FIG. 1 is a plan view of a mouth guard according to the invention.

The mouth guard disclosed in the drawing is made in its entirety of nonrigid plastic and comprises a U-shaped portion 10 and a major protruding flange 11A at one end of portion 10 and a minor protruding flange 11B at the other end of portion 10. Flange 11A is intended to be located behind the patient's teeth or palate while flange 11D is intended to be located in front of the patient's teeth or palate. When the mouth guard in located between the yaws of the patient it is prevented from forward and rearward displacement by the flanges. Portion 10 forms a through opening shaped as a keyhole comprising a wider portion 12A and a narrower portion 12B defined by two axial ribs 13 and opening at one side of the mouth guard.

The mouth guard described can be passed over an instrument that has already been introduced into the patient through his mouth, by pressing the instrument into the keyhole through the narrower portion 12B of the keyhole i.e. the slot defined by the ribs 13, under resilient yielding of the U-shaped portion 10. The instrument will be received by the wider portion 12A inwardly of the ribs and will be maintained therein centrally of the mouth guard as it will be prevented from sliding out of portion 12A by the ribs.

Since the mouth guard is made of nonrigid plastic damages on the patient and the instrument are avoided and the use of the mouth guard will be less uncomfortable to the patient.

What is claimed is:

1. A mouth guard for medical use comprising an U-shaped portion forming a through opening extending axially through the mouthguard to receive an instrument therein, said opening being shaped as a keyhole having a wider portion and a narrower portion forming a slot at one side of the mouth guard, extending along the total axial length thereof; and at each end of the U-shaped portion protruding radially from the outside surface of the U-shaped portion for positioning the mouth guard in the mouth said U-shaped portion and said flanges being made in their entirety of nonrigid plastic material to allow the instrument to be introduced laterally into the keyhole through the slot formed by the narrow portion under resilient yielding of the U-shaped portion and then to be received in the wider portion.

2. The mouth guard of claim 1 further comprising two axially extending ribs formed by the U-shaped portion, which define the narrower portion of the keyhole.

3. The mouthguard according to claim 2 wherein said mouthguard comprises resilient plastic.

4. The mouthguard according to claim 2, wherein said second ridge extends beyond the outer surface of said mouthguard body further than said first ridge.

5. The mouthguard according to claim 2, wherein said first and second opposed ribs are positioned adjacent said mouthguard second end.

6. The mouthguard according to claim 2, wherein said narrower portion of said body extends about half the length of said opening extending from said body first end to said body second end.

7. A mouth guard for medical applications, said mouthguard comprising:

(a) a body having an outer surface, an inner surface, a first end, and a second end, said mouthguard body having an opening extending through said body from said first end to said second end;

(b) a first ridge adjacent said mouthguard body first end;

(c) a second ridge adjacent said mouthguard body second end;

(d) first and second opposed ribs projecting from said body inner surface to form a narrower portion in said body opening, wherein said first and second opposed ribs form a keyhole shape in said opening allowing an instrument to be introduced through said mouthguard body opening and held in place by said opposed ribs.

* * * * *